United States Patent
Knippels et al.

(10) Patent No.: US 9,770,460 B2
(45) Date of Patent: *Sep. 26, 2017

(54) NON-DIGESTIBLE OLIGOSACCHARIDES FOR ORAL INDUCTION OF TOLERANCE AGAINST DIETARY PROTEINS

(71) Applicant: N.V. NUTRICIA, HM Zoetermeer (NL)

(72) Inventors: Léon Mathieu Johannes Knippels, WE Bunnik (NL); Elisabeth Catharina Adriana Maria van Esch, WH Utrecht (NL); Johan Garssen, DA Nieuwegein (NL)

(73) Assignee: N.V. NUTRICIA (NL)

( * ) Notice: Subject to any disclaimer, the term of this patent is extended or adjusted under 35 U.S.C. 154(b) by 2 days.

This patent is subject to a terminal disclaimer.

(21) Appl. No.: 14/995,345

(22) Filed: Jan. 14, 2016

(65) Prior Publication Data

US 2016/0129024 A1    May 12, 2016

Related U.S. Application Data

(60) Continuation of application No. 14/337,013, filed on Jul. 21, 2014, which is a division of application No. 13/700,790, filed as application No. PCT/EP2011/002699 on Jun. 1, 2011, now Pat. No. 9,119,838.

(30) Foreign Application Priority Data

Jun. 4, 2010   (WO) ................. PCT/EP2010/003374

(51) Int. Cl.
| | | |
|---|---|---|
| *A61K 38/10* | (2006.01) | |
| *A61K 38/16* | (2006.01) | |
| *A61K 31/702* | (2006.01) | |
| *A61K 31/733* | (2006.01) | |
| *A61K 38/01* | (2006.01) | |
| *A61K 38/17* | (2006.01) | |
| *A61K 39/35* | (2006.01) | |
| *A61K 39/00* | (2006.01) | |
| *A23L 33/00* | (2016.01) | |
| *A23L 33/17* | (2016.01) | |
| *A23L 33/18* | (2016.01) | |
| *A23L 33/185* | (2016.01) | |
| *A23L 33/19* | (2016.01) | |
| *A23L 33/21* | (2016.01) | |

(52) U.S. Cl.
CPC ............ *A61K 31/702* (2013.01); *A23L 33/17* (2016.08); *A23L 33/18* (2016.08); *A23L 33/185* (2016.08); *A23L 33/19* (2016.08); *A23L 33/21* (2016.08); *A23L 33/40* (2016.08); *A61K 31/733* (2013.01); *A61K 38/018* (2013.01); *A61K 38/10* (2013.01); *A61K 38/17* (2013.01); *A61K 39/0005* (2013.01); *A61K 39/35* (2013.01); *A23V 2002/00* (2013.01); *A61K 2039/577* (2013.01)

(58) Field of Classification Search
CPC ............ A23V 2002/00; A23V 2250/28; A23V 2250/5424; A23V 2250/54242; A23V 2250/54244; A23V 2250/54246; A23V 2250/54252; A23V 2250/548; A23V 2200/304; A23V 2200/324; A23L 33/17; A23L 33/18
See application file for complete search history.

(56) References Cited

U.S. PATENT DOCUMENTS

| | | | |
|---|---|---|---|
| 9,060,996 B2 * | 6/2015 | Knippels | .............. A61K 31/733 |
| 9,119,838 B2 * | 9/2015 | Knippels | .............. A61K 31/733 |
| 2009/0297545 A1 | 12/2009 | Gauthier et al. | |

FOREIGN PATENT DOCUMENTS

| | | | | |
|---|---|---|---|---|
| EP | 0629350 | * | 6/1994 | ............... A23J 3/34 |
| EP | 0 629 350 A1 | | 12/1994 | |
| EP | 0 827 697 A1 | | 3/1998 | |
| EP | 1 557 096 A1 | | 7/2005 | |
| EP | 1 112 006 A2 | | 6/2007 | |
| EP | 2 044 851 A1 | | 4/2009 | |
| WO | WO 00/42863 | | 7/2000 | |
| WO | WO 01/41581 A1 | | 6/2001 | |
| WO | WO 2005/039597 A2 | | 5/2005 | |
| WO | WO 2006/130204 A1 | | 3/2006 | |
| WO | WO 2007/004878 A2 | | 1/2007 | |
| WO | WO 2008/056983 A1 | | 11/2007 | |
| WO | WO 2008/016306 A1 | | 2/2008 | |
| WO | WO2008/153391 | * | 12/2008 | ............... A23L 1/30 |
| WO | WO 2009/040310 A1 | | 4/2009 | |
| WO | WO 2009/095240 A1 | | 8/2009 | |
| WO | WO2009/151315 | * | 12/2009 | |
| WO | WO2009/151331 | * | 12/2009 | ........... A61K 31/702 |

OTHER PUBLICATIONS

Savino, European Journal of Clinical Nutrition (2006) 60:1304-1310.*
Savino, et al., "Reduction of crying episodes owing to infantile colic: a randomized controlled study on the efficacy of a new infant formula," European Journal of Clinical Nutrition, 2006, 60: 1304-1310.
P. González-Tello et al, 1994, "Enzymatic Hydrolysis of Whey Proteins II. Molecular-Weight Range." Biotechnology and Bioengineering, vol. 44, pp. 529-532 (1994).
L. Prosky et al, "Determination of Insoluble, Soluble, and Total Dietary Fiber in Foods and Food Products: Interlaboratory Study," J. Assoc. Off. Anal. Chem., vol. 71, No. 5, pp. 1017-1023 (1988).
B. Ruiter et al, "Characterization of T cell epitopes in αs1-casein in cow's milk allergic, atopic and non-atopic children," Clinical and Experimental Allergy, 36, pp. 303-310 (2006).
International Search Report dated Sep. 5, 2011 issued in corresponding International Application No. PCT/EP2011/002699.

(Continued)

*Primary Examiner* — Marcela M Cordero Garcia
(74) *Attorney, Agent, or Firm* — Ostrolenk Faber LLP

(57) ABSTRACT

Compositions and methods for providing infant nutrition with partially hydrolysed proteins and non-digestible oligosaccharides for use in induction of oral tolerance against native dietary proteins.

24 Claims, No Drawings

(56) References Cited

OTHER PUBLICATIONS

Verlinden et al.: "The effects of inulin supplementation of diets with or without hydrolysed protein sources on digestibility, faecal characteristics, haematology and immunoglobulins in dogs", British Journal of Nutrition, vol. 96, 2006, pp. 936-944, XP002623528.
Savino et al.: "Reduction of crying episodes owing to infantile colic: a randomized controlled study on the efficacy of a new infant formula", European Journal of Clinical Nutrition, vol. 60, 2006, pp. 1304-1310, XP002623529.
De Freitas et al.: "Characterization of Protein Hydrolysates Prepared for Enteral Nutrition", J. Adri. Food Chem., vol. 41, 1993, pp. 1432-1438, XP002623530.
Francesco Savino et al.: "Advances in the management of digestive problems during the first months of life", Acta Paediatrica. Supplement Universitetsforlaget, Oslo, NO, vol. 94, No. S449, Jan. 1, 2005, pp. 120-124, XP002511772.
H. Schmelzle et al.: "Randomized Double-blind Study of the Nutritional Efficacy and Bifidogenicity of a New Infant Formula Containing Partially Hydrolyzed Protein, a High β-Palmitic Acid Level, and Nondigestible Oligosaccharides", Journal of Pediatric Gastroenterology and Nutrition, Raven Press, New York, NY, US, vol. 36, No. 3, Mar. 1, 2003, pp. 343-351, XP008033738.
Database Caplus [Online] Chemical Abstracts Service, Columbus, Ohio, US; XP002656832, retrieved from stn Database accession No. 2008:1039575 abstract & JP 2008 195618 A, Aug. 28, 2008.
Yvan Vandenplas: "Infant Formula With Partial Protein Hydrolysates: Evidence and Remaining Questions", Journal of Pediatric Gastroenterology and Nutrition, vol. 50, No. 4, Apr. 2010.
International Preliminary Report on Patentability issued in corresponding International Patent Application No. PCT/EP2011/002699.
Mussatto, et al. (Carbohydrate Polymers (2007) 68: 587-597).
Savino, European Journal of Clinical Nutrition (2006) 60: 1304-1310.
Chinese Second Office Action dated Sep. 2, 2014 in corresponding Chinese Patent Application No. 2014082800568990 (with English language translation)(14 pages).
Donna M. Roberts, et al., "Infantile Colic," American Family Physician, vol. 70, No. 4, Aug. 15, 2004, pp. 735-740.

* cited by examiner

SEQUENCE LISTING

```
<160> NUMBER OF SEQ ID NOS: 9

<210> SEQ ID NO 1
<211> LENGTH: 18
<212> TYPE: PRT
<213> ORGANISM: Bos primigenius

<400> SEQUENCE: 1

Gln Lys Val Ala Gly Thr Trp Tyr Ser Leu Ala Met Ala Ala Ser Asp
1               5                   10                  15

Ile Ser

<210> SEQ ID NO 2
<211> LENGTH: 18
<212> TYPE: PRT
<213> ORGANISM: Bos primigenius

<400> SEQUENCE: 2

Trp Tyr Ser Leu Ala Met Ala Ala Ser Asp Ile Ser Leu Leu Asp Ala
1               5                   10                  15

Gln Ser

<210> SEQ ID NO 3
<211> LENGTH: 18
<212> TYPE: PRT
<213> ORGANISM: Bos primigenius

<400> SEQUENCE: 3

Ala Ala Ser Asp Ile Ser Leu Leu Asp Ala Gln Ser Ala Pro Leu Arg
1               5                   10                  15

Val Tyr

<210> SEQ ID NO 4
<211> LENGTH: 18
```

```
<212> TYPE: PRT
<213> ORGANISM: Bos primigenius

<400> SEQUENCE: 4

Leu Leu Asp Ala Gln Ser Ala Pro Leu Arg Val Tyr Val Glu Glu Leu
1               5                   10                  15

Lys Pro

<210> SEQ ID NO 5
<211> LENGTH: 18
<212> TYPE: PRT
<213> ORGANISM: Bos primigenius

<400> SEQUENCE: 5

Lys Val Leu Val Leu Asp Thr Asp Tyr Lys Lys Tyr Leu Leu Phe Cys
1               5                   10                  15

Met Glu

<210> SEQ ID NO 6
<211> LENGTH: 18
<212> TYPE: PRT
<213> ORGANISM: Bos primigenius

<400> SEQUENCE: 6

Thr Asp Tyr Lys Lys Tyr Leu Leu Phe Cys Met Glu Asn Ser Ala Glu
1               5                   10                  15

Pro Glu

<210> SEQ ID NO 7
<211> LENGTH: 18
<212> TYPE: PRT
<213> ORGANISM: Bos primigenius

<400> SEQUENCE: 7

Leu Leu Phe Cys Met Glu Asn Ser Ala Glu Pro Glu Gln Ser Leu Ala
1               5                   10                  15

Cys Gln

<210> SEQ ID NO 8
<211> LENGTH: 18
<212> TYPE: PRT
<213> ORGANISM: Bos primigenius

<400> SEQUENCE: 8

Ala Leu Lys Ala Leu Pro Met His Ile Arg Leu Ser Phe Asn Pro Thr
1               5                   10                  15

Gln Leu

<210> SEQ ID NO 9
<211> LENGTH: 18
<212> TYPE: PRT
<213> ORGANISM: Bos primigenius

<400> SEQUENCE: 9

Met His Ile Arg Leu Ser Phe Asn Pro Thr Gln Leu Glu Glu Gln Cys
1               5                   10                  15

His Ile
```

NON-DIGESTIBLE OLIGOSACCHARIDES FOR ORAL INDUCTION OF TOLERANCE AGAINST DIETARY PROTEINS

CROSS-REFERENCE TO RELATED APPLICATIONS

The present application is a continuation of prior U.S. patent application Ser. No. 14/337,013, filed Jul. 21, 2014, by Léon Mathieu Johannes Knippels, Elisabeth Catharina Adriana Maria Van Esch and Johan Garssen, entitled "NON-DIGESTIBLE OLIGOSACCHARIDES FOR ORAL INDUCTION OF TOLERANCE AGAINST DIETARY PROTEINS," which is a divisional of U.S. patent application Ser. No. 13/700,790, filed Nov. 29, 2012, now U.S. Pat. No. 9,119,838, issued Sep. 1, 2015, the entire contents of which are incorporated herein by reference. U.S. patent application Ser. No. 13/700,790 is a 35 U.S.C. §371 National Phase conversion of International Application No. PCT/EP2011/002699, filed Jun. 1, 2011, which claims the benefit of International Application No. PCT/EP2010/003374, filed Jun. 4, 2010, the entire contents of which are incorporated herein by reference.

FIELD

The invention relates to an enteral composition containing a non-digestible oligosaccharide and a partial protein hydrolysate, which can induce oral immunological tolerance to the native proteins in the diet, in particular to milk proteins.

BACKGROUND

During the common process of nutrition dietary proteins are presented to the immune system via the gastro-intestinal tract without an immune response to the ingested nutrients. This unresponsiveness is called oral immune tolerance or oral tolerance. The induction of oral immune tolerance is especially relevant for infants, who after birth are exposed for the first time to dietary proteins and have to adapt to this. If in infants oral immune tolerance is not established, food allergy will occur. Persons suffering from food allergy require a diet in which the specific food protein is avoided.

For infants suffering from allergy to cow's milk protein infant formulae are on the market comprising extensively hydrolysed proteins (extensive protein hydrolysate) or even merely free amino acids as nitrogen source. In these formulae no allergenic protein or peptides are present.

Infants born from parents of whom one or both suffers from an atopic disease, or who have one or more siblings suffering from an atopic disease, have a higher risk of becoming allergic to dietary proteins. For this group, besides the preferred breast feeding, hypoallergenic formulae are on the market, comprising a partial protein hydrolysate (partially hydrolysed proteins). These partially hydrolysed proteins have a decreased allergenicity. This approach has been demonstrated to be efficient in order to prevent sensitization by native proteins present in the adapted formulae. Typically, the extent of hydrolysis of proteins is less than those of extensively hydrolysed proteins for babies already suffering from allergy. These formulations have the advantage that they not only reduce the risk of developing an allergic response by preventing sensitization to the protein, but also induce orally an immunological tolerance to the intact protein. This has the advantage that later on the native protein can be introduced in the diet, with a reduced risk on allergic reactions.

EP 1 557 096 discloses infant food with low-allergenic casein hydrolysate and probiotic strains of lactic acid bacteria. For tolerance induction a partial whey protein hydrolysate is preferred.

EP 2 044 851 discloses a nutritional composition with partially hydrolysed milk protein having a degree of hydrolysis between 15% and 25% and 50 to 1000 ng of TGF-beta per 100 ml for the primary prevention of allergic reactions to dietary protein and the prevention of development of atopic diseases in young mammals.

EP 0 629 350 discloses the use of non-allergenic whey protein hydrolysates which are said to be capable of inducing cow's milk protein tolerance.

EP 0 827 697 discloses the use of whey, that has been hydrolysed enzymatically for the preparation of compositions that induce oral tolerance to cows' milk in susceptible mammals. The whey has a level of immunological detection of allergenic proteins>=100 times less than that of unhydrolysed whey.

WO 00/42863 discloses a hypoallergenic composition for the induction of protein tolerance in at risk infants of protein allergy, comprising a non allergenic protein extensively hydrolysed basis and/or a free amino acid basis, said composition comprising as the active ingredient at least one tolerogenic peptide of the allergenic protein.

However, the hypoallergenic compositions of the prior art often provide their effects just by avoiding the presence of potential allergens thereby providing only a secondary prevention effect and/or they require the presence of special ingredients such as probiotics or growth factors.

Still there is a need for nutrition for subjects at risk of developing or suffering from food allergy with improved effects on immune tolerance induction.

Thus, the technical problem underlying the present invention is to provide compositions, methods and means for overcoming the above-identified disadvantages, in particular an improved oral tolerance, in particular providing an improved primary allergy-preventing effect, against dietary proteins in humans, in particular humans at risk for developing a food allergy.

SUMMARY OF THE INVENTION

The present inventors found that the capacity of a partial milk protein hydrolysate to induce oral immune tolerance was synergistically and significantly increased when concomitantly non-digestible oligosaccharides were also administered via the diet. It was found that mice, which were sensitized to intact whey protein, showed an acute allergic skin response after an intradermal challenge with intact whey protein. This response was reduced after an intradermal challenge with either extensively or partially hydrolysed whey protein. In case these sensitized mice were pretreated by oral administration of partial whey protein hydrolysate or with intact whey protein prior to sensitisation a significantly reduced acute skin response to intact intradermal whey protein was observed. This reduction of the response effect was not observed when as a pretreatment extensive whey protein hydrolysate was orally administered.

Surprisingly, it was observed that when during the pretreatment with partial whey protein hydrolysate the mice were also pretreated with non-digestible oligosaccharides, the acute skin response was synergistically further reduced. The present invention, in particular the use of the non-digestible oligosaccharides to potentiate the effect of the partial protein hydrolysate, could even achieve a complete abolishment of the acute skin response. This enhanced and therefore improved effect on induction of oral immune tolerance due to the presence of the non-digestible oligosaccharides was not observed after a pretreatment with a diet with non-digestible oligosaccharides (hereinafter also called NDO) alone or after a pretreatment with extensive whey protein hydrolysate and a diet comprising NDO. Therefore, the present invention provides a composition comprising a combination of a partial protein hydrolysate, in particular a partial whey protein hydrolysate, and non-digestible oligosaccharides, in particular galacto-oligosaccharides, fructo-oligosaccharides and/or uronic acid oligosaccharides, preferably for use in the enhanced induction of tolerance against dietary proteins, in particular against milk protein, more particular whey protein, preferably in humans. The present composition is especially beneficial for use in infants, more preferably in infants at risk of developing food allergy.

Further, according to the present invention specific sequences of specific peptides of the whey protein beta-lactoglobulin were identified, which are capable of inducing oral immune tolerance against intact whey protein if administered as a pretreatment to mice sensitized to intact whey protein. This effect was synergistically enhanced by concomitant pretreatment with non-digestible oligosaccharides.

DETAILED DESCRIPTION

Thus, the present invention solves its technical problem in particular by providing the teaching to use a non-digestible oligosaccharide for enhancing the oral tolerance inducing effect of a partial protein hydrolysate of the present invention against dietary proteins, preferably wherein the partial protein hydrolysate is characterised in that it comprises at least 3 wt % of peptides with a size of 5 kDa or above and at least 50 wt. % of peptides with a size below 5 kDa.

The technical problem is also solved by providing the teaching to use a non-digestible oligosaccharide for enhancing the primary allergy preventing effect of a partial protein hydrolysate of the present invention against dietary proteins, preferably wherein the partial protein hydrolysate is characterised in that it comprises at least 3 wt. % of peptides with a molecular weight of 5 kDa or above and at least 50 wt. % of peptides with a size below 5 kDa.

Preferably, the non-digestible oligosaccharides for enhancing the oral tolerance inducing effect of a partial protein hydrolysate or for enhancing the primary allergy-preventing effect of a partial protein hydrolysate are contained together with the partial protein hydrolysate in an enteral composition of the present invention.

Thus, the present invention solves its technical problem also by the provision of an enteral composition comprising at least one non-digestible oligosaccharide and at least one partial protein hydrolysate of the present invention for use in the, preferably enhanced, induction of oral tolerance against dietary proteins, preferably the partial protein hydrolysate being characterized in that it comprises at least 3 wt. % of peptides with a molecular weight of 5 kDa or above and at least 50 wt. % of peptides with a size below 5 kDa.

The present invention solves its technical problem also by providing an enteral composition comprising at least one non-digestible oligosaccharide and at least one partial protein hydrolysate for use in the prevention of food allergy or inflammatory bowel disease, the partial protein hydrolysate being characterized in that it comprises at least 3 wt. % of peptides with a size of 5 kDa or above and at least 50 wt. % of peptides with a size below 5 kDa.

The present invention solves its technical problem also by providing an enteral composition, wherein the non-digestible oligosaccharide is a mixture of galacto-oligosaccharides, fructo-oligosaccharides and galacturonic acid oligosaccharides.

The present invention solves its technical problem also by providing an enteral composition, wherein the partial protein hydrolysate is partial whey protein hydrolysate and wherein the non-digestible oligosaccharide is a mixture of galacto-oligosaccharides, fructo-oligosaccharides and galacturonic acid oligosaccharides.

The present invention solves its underlying problem also by the provision of a process for the preparation of an enteral composition with an, preferably enhanced, oral tolerance-inducing effect, wherein at least one partial protein hydrolysate of the present invention, preferably a partial protein hydrolysate comprising at least 3 wt. % of peptides with a molecular weight of 5 kDa or above and at least 50 wt. % of peptides with a size below 5 kDa, and at least one non-digestible oligosaccharide are mixed and the enteral composition with an, preferably enhanced, oral tolerance-inducing effect is obtained. The present invention also relates to a process for the preparation of an enteral composition with an, preferably enhanced, oral tolerance-inducing effect, wherein at least one beta-lactoglobulin peptide and at least one non-digestible oligosaccharide are mixed and the enteral composition with an, preferably enhanced, oral tolerance-inducing effect is obtained.

In a furthermore preferred embodiment of the present invention a method to feed a subject, in particular an infant, is provided, preferably a method to treat, in particular prevent, allergy, preferably food allergy, and/or atopic diseases, including atopic eczema and/or asthma and/or rhinitis and/or dermatitis said method comprising administering the present enteral composition to a subject in need thereof, in particular an infant, in particular an infant at risk of developing such a disease.

Thus, the present invention is inter alia based on the surprising and advantageous finding that a non-digestible oligosaccharide is useful for improving, that means enhancing, the oral tolerance-inducing effect of a partial protein hydrolysate. In particular, the present invention teaches to use a non-digestible oligosaccharide for improving, that means enhancing, the oral tolerance-inducing effect of a partial protein hydrolysate and thereby also improving, that means enhancing, the primary allergy-preventing effect of a partial protein hydrolysate.

The present invention is in particular advantageous in so far as it provides an oral tolerance and a primary allergy-preventing effect which is at least as good and effective as using intact whey protein for inducing tolerance and preventing allergy whereas, however, the risk of provoking allergic responses is much less when using the partial protein hydrolysate combined with the NDOs according to the present invention.

In the context of the present invention an enhancement is meant to be an increase, in particular a significant increase, from a given measurable basic value to a measurable value significantly above the basic value.

In the context of the present invention an enhancement of a partial protein hydrolysate-induced oral tolerance is measured according to example 1 of the present teaching in the given mouse model to determine oral tolerance to proteins. Accordingly, a state of a partial protein hydrolysate-induced oral tolerance useful as a basic value is indicated by an immediate type hyperresponsiveness (ITH) of 35 to 90% of a non-induced oral tolerance having an ITH value of 100%.

A significant enhancement of said induced oral tolerance is characterised by an immediate type hyperresponsiveness of 0 to 30%, preferably 0 to 25%, preferably 0 to 20%, preferably 0 to 10%, most preferably 0% of the non-induced oral tolerance having an ITH value of 100%. Thus, an enhancement of an induced oral tolerance preferably means at least 15%, at least 20%, at least 30%, at least 40%, at least 50%, at least 60%, at least 70%, at least 80%, at least 90% and preferably 100% reduction of the basic value of an induced oral tolerance, indicated by an immediate type hyperresponsiveness measured in the mouse model test as given above.

The relative value for the ITH translates into the oral tolerance value by the following calculation formula: 100 minus ITH=tolerance value. Thus, most preferably an enhancement of a partial protein hydrolysate-induced oral tolerance leads to a full tolerance, that means a 60 to 100%, preferably 90 to 100%, preferably 95 to 100%, most preferably 100% tolerance, against dietary proteins.

In the context of the present invention an enhancement of a primary allergy preventing effect of a partial protein hydrolysate is measured according to example 1 of the present teaching in the given mouse model to determine oral tolerance to proteins. Accordingly, a state of a primary allergy-preventing effect of a partial protein hydrolysate—useful as a basic value is indicated by an immediate type hyperresponsiveness (ITH) of 35 to 90% of a fully developed allergy state having an ITH value of 100%. A significant enhancement of said primary allergy-preventing effect is characterised by an immediate type hyperresponsiveness of 0 to 30%, preferably 0 to 25%, preferably 0 to 20%, preferably 0 to 10%, most preferably 0% of a fully developed allergy state having an ITH value of 100%. Thus, an enhancement of an primary allergy-preventing effect preferably means at least 15%, at least 20%, at least 30%, at least 40%, at least 50%, at least 60%, at least 70%, at least 80%, at least 90% and preferably 100% reduction of the basic value of the partial protein hydrolysate caused primary allergy-preventing effect indicated by immediate type hyperresponsiveness measured in the mouse model test as given above. Thus, most preferably an enhancement of a primary allergy-preventing effect of a partial protein hydrolysate leads to a full primary allergy prevention, that means a 90 to 100%, preferably 95 to 100%, most preferably 100% tolerance, against dietary proteins.

In the context of the present invention a primary allergy prevention, which is based on a primary allergy-preventing effect, is a prophylactic treatment for the purpose of partially, preferably totally, preventing the development and breaking out of symptoms of an allergy in a subject at risk or even high risk. In the context of the present invention the primary allergy-preventing effect is an immune system-modulating effect. The primary allergy-preventing effect is not including a secondary allergy-preventing effect caused by the avoidance of allergising food ingredients from the diet.

In the context of the present invention the term "5 kDa or above" means "at least 5 kDa". In the context of the present invention the term "below 5 kDa" means up to but excluding 5 kDa.

In the context of the present invention the term "oral tolerance" preferably means oral immune tolerance.

The present invention further relates in a further embodiment to an enteral composition comprising at least one non-digestible oligosaccharide and at least one specific mammalian milk protein peptide, preferably a specific whey protein peptide, more preferably a specific beta-lactoglobulin peptide, for use in the induction of oral tolerance against dietary proteins. The present invention further relates in a preferred embodiment to an enteral composition comprising at least one non-digestible oligosaccharide and at least one specific mammalian milk protein peptide, preferably a specific whey protein peptide, more preferably a specific beta-lactoglobulin peptide, for use in the prevention of food allergy or inflammatory bowel disease.

The at least one specific beta-lactoglobulin peptide contained in the enteral composition can be a natural or a synthetic peptide. Preferably, the specific peptide, in particular the specific beta-lactoglobulin peptide consists of 12 to 38, more preferably 15 to 36 amino acids, even more preferably 18 to 34, most preferably 18 amino acids, of the beta-lactoglobulin amino acid sequence. Without wishing to be bound by theory, it is believed that a lower size of the peptides will result in less oral tolerance induction, because the tolerance inducing epitope then is presented in a less optimal way to the T cell. A higher size on the other hand increases the risk on allergic reactions, since the chance on cross linking two IgE molecules on a mast cell increases with increasing size.

Preferably, the at least one specific beta-lactoglobulin peptide present in these preferred enteral compositions comprises a sequence, in particular an amino acid sequence, selected from the group consisting of SEQ ID NO 1, SEQ ID NO 2, SEQ ID NO 3 and SEQ ID NO 4. Most preferred, the enteral composition comprises a mixture comprising two, three or preferably four peptides comprising the SEQ ID NOs 1 to 4. Each of these peptides can preferably be substituted at its C- and/or N-terminus independently each with 1 to 10 amino acids, preferably 1 to 8 amino acids, more preferably 1 to 5 amino acids, which can be any amino acids. The specific beta-lactoglobulin peptide preferably has a molecular weight of below 5 kDa, in particular from 0.1 to 4.9 kDa, preferably from 0.5 to 4.9 kDa, preferably 2 to 4.9 kDa, most preferred of 2.4 kDa.

Surprisingly, it was found that mice, which were sensitized to intact whey protein, showed a significantly reduced acute skin response to intact intradermal whey protein when as a pretreatment a mixture of the peptides with the SEQ ID NOs 1 to 4 was administered. It was further observed that when during the pretreatment with the peptide mixture the mice were also pretreated with non-digestible oligosaccharides, the acute skin response was synergistically further reduced.

The present invention also relates in a preferred embodiment to non-digestible oligosaccharides for use in the enhancement of oral tolerance against dietary proteins, wherein the oral tolerance is induced by at least one beta-lactoglobulin peptide comprising a sequence selected from the group consisting of SEQ ID NO 1, SEQ ID NO 2, SEQ ID NO 3 and SEQ ID NO 4, wherein the peptide preferably has a molecular weight of below 5 kDa.

The present invention also relates in a preferred embodiment to non-digestible oligosaccharides for use in the enhancement of a primary allergy preventing effect of at least one beta-lactoglobulin peptide comprising a sequence selected from the group consisting of SEQ ID NO 1, SEQ ID NO 2, SEQ ID NO 3 and SEQ ID NO 4, wherein the peptide preferably has a molecular weight of below 5 kDa.

Partial Protein Hydrolysate of the Present Invention

The present composition comprises partial protein hydrolysate, hereinafter also called "partially hydrolysed protein". Preferably, the present composition does not comprise intact, non-hydrolysed protein. Intact, non-hydrolysed protein has a too high allergenicity and may disadvantageously evoke an allergic reaction. The present composition may in a preferred embodiment further, besides partial protein hydrolysate, comprise extensively hydrolysed protein, also called extensive protein hydrolysate, and/or free amino acids. Extensively hydrolysed protein and/or free amino acids do not evoke an allergic reaction, but also do not have oral tolerance inducing properties.

Preferably, partial protein hydrolysate is derived from mammalian milk, more preferably cow's milk. Human milk protein is preferably excluded from the present invention. Preferably, the partial protein hydrolysate comprises or is partial mammalian milk protein hydrolysate. More preferably, the partial protein hydrolysate comprises or is partial whey protein hydrolysate. More preferably, the partial protein hydrolysate comprises or is partial beta-lactoglobulin hydrolysate and/or partial alpha-lactalbumin hydrolysate. In another embodiment of the present invention, the partial protein hydrolysate comprises or is partial pea, soy and/or rice protein hydrolysate. More preferably, the partial protein hydrolysate comprises or is partial casein hydrolysate.

The protein to be partially hydrolysed to obtain the partial protein hydrolysate of the present invention may be any composition containing a protein, preferably a milk protein, and is in particular a solution or dispersion, preferably of milk proteins. Preferably, the protein to be partially hydrolysed is whey protein, acid whey protein, sweet whey protein, whey protein concentrate, whey protein isolate, demineralized whey powder or caseinates.

The proteolytic enzymes used for the partial hydrolysis may be for example, from animal or vegetable origins (pepsin, chymotrypsin, trypsin, intestinal mucosa extract, pancreatic extracts, chymosin, papain, bromelain, ficin), bacterial or fungi origins (serine and metalloproteases from *Bacillus subtilis, Bacillus licheniformis, Aspergillus orysae, Aspergillus wentii* and acidic proteases from *Aspergillus orizae, Aspergillus wentii, Mucor miehei, Mucor pusillus, Endothia parasitica*) or a combination of these.

During hydrolysis, the concentration of the protein in solution or in suspension is preferably around 5-20% by weight (wt %) and could be pasteurised before introducing proteases. The ratio enzyme/protein may be 0.1-10% weight/weight and preferably of about 0.25 to 4%.

Hydrolysis may be conducted at a temperature of about 35° C. to 65° C., during 30 minutes to 10 hours, preferably 30 min to 4 hours at pH values within the range 2.5 to 11, preferably 4.5, to 7.0, 8.0, and 8.5. If desired the pH of the solution can be adjusted and regulated with citric acid, food grade HCl or NaOH, $NH_4OH$, KOH, $Ca(OH)_2$ for instance at a concentration of 2N pure or in blend.

The enzymatic process of hydrolysis may be stopped by fast cooling.

Then, the protein hydrolysate may be subjected to a heat treatment of about 0.1 to 10 min at a temperature of about 70 to 110° C. to inactivate residual enzymes, i.e. proteases.

The protein hydrolysate solution thus obtained can be clarified by centrifugation or filtration to remove insoluble and intact proteins respectively, and a clear solution is recovered. It is possible to use at industrial scale different type of membranes (spiral, tubular, flat, allow fibbers) made with different materials (minerals, polysulfone). Depending on the type of enzyme, the hydrolysis conditions and the type of filtration, e. g. the membranes used, the desired peptide size distribution of the partial protein hydrolysate is obtained at this step.

The recovered clear hydrolysate solution can, if desired, be concentrated by evaporation to a dry solid content of for instance 10-50% for a subsequent treatment or spray dried.

The present composition preferably contains a partial protein hydrolysate with a degree of hydrolysis of the protein of 5 to 25%, more preferably of 7.5 to 21%, most preferably of 10 to 20%. The degree of hydrolysis is defined as the percentage of peptide bonds which have been broken down by enzymatic hydrolysis, with 100% being the total potential peptide bonds present. Proteins with the above-mentioned degree of hydrolysis provide sufficient peptides with a chain length of 2 to 30.

In the following, wt % values (relative amount) of peptides are based on dry weight of peptides in relation to dry weight of total partial protein hydrolysate, if not otherwise indicated.

The peptide size and molecular weight distribution can be determined by routine methods known to the skilled person such as HPLC or size exclusion chromatography (SEC), in particular high performance size exclusion chromatography. A suitable method is disclosed in González-Tello et al, 1994, Enzymatic hydrolysis of whey proteins II. Molecular weight range. Biotech. Bioeng, 44, 529-532.

In a preferred embodiment of the present invention the partial protein hydrolysate is characterised in that it comprises at least 3 wt % of peptides with a size of 5 kDa or above, preferably at least 3.5 wt % of peptides with a size of 5 kDa or above, preferably at least 4 wt %, more preferably at least 4.5 wt % of peptides with a size of 5 kDa or above. The partial protein hydrolysate of the present invention is further characterised in that at least 50 wt %, preferably at least 55 wt %, preferably at least 60 wt %, preferably at least 70 wt % of peptides have a size below 5 kDa.

More preferably, the partial protein hydrolysate comprises at least 0.5 wt %, preferably at least 1 wt. %, preferably at least 1.5 wt % and most preferably at least 2 wt % of peptides with a size above 20 kDa. More preferably, the partial protein hydrolysate comprises at least 0.5 wt %, preferably at least 1 wt %, preferably at least 1.5 wt %, preferably at least 2 wt % to at most 3.5 wt %, preferably at most 3.0 wt % peptides with a size above 20 kDa.

In a furthermore preferred embodiment, the partial protein hydrolysate comprises at least 5 wt %, preferably 5 to 10 wt %, preferably 6 to 10 wt % of peptides with a size of at least 3 kDa.

Preferably, the partial protein hydrolysate of the present invention is characterised by a ratio of the relative amount of peptides with a size from 2 to <5 kDa to the relative amount of peptides with a size of at least 5 kDa of (5 to 1):1, preferably (4 to 1):1, preferably (3 to 1):1, preferably (2 to 1):1, preferably 1:1.

In a furthermore preferred embodiment of the present invention the partial protein hydrolysate comprises at least 0.5 wt %, preferably at least 0.6 wt %, in particular 0.5 to 3.0 wt %, preferably 0.5 to 2.0 wt %, preferably 0.5 to 1.0 wt % of peptides with a size of 10 to 20 kDa.

Preferably, the partial protein hydrolysate of the present invention is characterised by a ratio of the relative amount of peptides with a size from 5 to 10 kDa to the relative amount of peptides with a size of more than 20 kDa of (5 to 1):(1 to 5), preferably (3 to 1):(1 to 3), more preferably (2 to 1):(1 to 2), in particular 1:1.

In a furthermore preferred embodiment the partial protein hydrolysate of the present invention is particularly characterised by a molecular size distribution of its peptides, wherein the relative weight amount of peptides with a size of above 20 kDa is higher, in particular at least two times higher, than the relative amount of peptides with a size of 10 to 20 kDa. Thus, in a preferred embodiment of the present invention the partial protein hydrolysate is characterised by a ratio of the relative amount of peptides with a size from 10 to 20 kDa to the relative amount of peptides with a size above 20 kDa of 1:(1.1 to 3), preferably 1:(1.1 to 2.5), preferably 1:(1.5 to 2).

In a furthermore preferred embodiment of the present invention the partial protein hydrolysate of the present invention is characterised in that the relative amount of peptides with a size from 10 to 20 kDa is lower than the relative amount of peptides with a size of more than 20 kDa and lower than the relative amount of peptides with a size from 5 to 10 kDa. Thus, in a particularly preferred embodiment the partial protein hydrolysate is characterised by a special distribution of the peptides, in particular of the peptides with a size of at least 5 kDa, in particular by a distribution, wherein both the amounts of peptides with a size of above 20 kDa and of peptides with a size from 5 to 10 kDa is higher than the relative amount of peptides with a size from 10 to 20 kDa, and wherein preferably at least 50 wt %, most preferably at least 60 wt % of peptides, have a size below 5 kDa.

In a preferred embodiment the partial protein hydrolysate is being characterised in that the hydrolysate comprises peptides with the following size distribution: 60 to 90 wt % with a size<1 kDa, 5 to 20 wt % of peptides with a size of 1 to <2 kDa, 2 to 15 wt % of peptides with a size of 2 to <5 kDa, 0.6 to 3 wt % of peptides with a size of 5 to <10 kDa, 0.5 to 2 wt % of peptides with a size 10 to 20 kDa and 1 to 3 wt % of peptides with a size>20 kDa.

In a preferred embodiment the partial protein hydrolysate is being characterised in that the hydrolysate comprises peptides with the following size distribution: 85 to 90 wt % peptides with a size<1 kDa, 6 to 10 wt % of peptides with a size 1 to <2 kDa, 2 to 6 wt % of peptides with a size 2 to <5 kDa, 0.6 to 3 wt % of peptides with a size 5 to <10 kDa, 0.5 to 2 wt % of peptides with a size 10 to 20 kDa and 1 to 3 wt % of peptides with a size>20 kDa.

In a preferred embodiment the partial protein hydrolysate is being characterised in that the hydrolysate comprises peptides with the following size distribution: 85 wt. %<1 kD, 8 wt. % 1 to <2 kDa, 4 wt. % 2 to <5 kDa, 1 wt. % 5 to <10 kDa, 0.6 wt. % 10 to 20 kDa and 1.4 wt. %>20 kDa.

In a preferred embodiment, the partial whey protein hydrolysate comprises at least one specific mammalian milk protein peptide, preferably a specific whey protein peptide, more preferably a specific beta-lactoglobulin peptide. The at least one specific beta-lactoglobulin peptide contained in the enteral composition can be a natural or a synthetic peptide. Preferably, the specific peptide, in particular the specific beta-lactoglobulin peptide consists of 12 to 38, more preferably 15 to 36 amino acids, even more preferably 18 to 34 amino acids, most preferably 18 amino acids, of the beta-lactoglobulin amino acid sequence. The specific beta-lactoglobulin peptides preferably have a size of below 5 kDa, in particular of 0.1 to 4.9 kDa, preferably from 0.5 to 4.9, more preferably of 2 to 4.9 kDa, most preferred of about 2.4 kDa.

Preferably, the at least one specific beta-lactoglobulin peptide present in these preferred enteral compositions comprises a sequence selected from the group consisting of SEQ ID NO 1, SEQ ID NO 2, SEQ ID NO 3 and SEQ ID NO 4. Most preferred, the enteral composition comprises a mixture comprising two, three or preferably four peptides comprising the SEQ ID NOs 1 to 4. Each of these peptides can preferably be substituted at its C- and/or N-terminus independently each with 1 to 10 amino acids, preferably 1 to 8 amino acids, more preferably 1 to 5 amino acids, which can be any amino acids.

Thus, the present invention relates in a preferred embodiment to an enteral composition comprising at least one non-digestible oligosaccharide and at least one partial protein hydrolysate comprising specific beta-lactoglobulin peptides comprising a sequence selected from the group consisting of SEQ ID NO 1, SEQ ID NO 2, SEQ ID NO 3 and SEQ ID NO 4.

However, it is also foreseen in a further embodiment of the present invention that the specific beta-lactoglobulin peptides are not part of a partial whey protein hydrolysate, but in particular are the only protein source used or they are used together with components other than a partial whey protein hydrolysate such as free amino acids or an extensively hydrolysed protein. Typically, extensive protein hydrolysates have a free amino acid content of above 10 g per 100 g protein. Preferably, the term protein as used here includes peptides and free amino acids.

The non-digestible oligosaccharide used in the enteral composition or for use together with the specific beta-lactoglobulin peptides is preferably a mixture of galacto-oligosaccharides, fructo-oligosaccharides and galacturonic acid oligosaccharides.

Preferably, the at least one specific beta-lactoglobulin peptide is present in the enteral composition in a concentration of at least 100 mg, more preferably at least 120 mg, in particular 150 mg, each per 100 ml.

In a preferred embodiment of the present invention the present enteral composition preferably comprises at least 7 wt %, more preferably at least 8 wt %, preferably at least 9 wt %, preferably 7 to 40 wt %, more preferably 7 to 20 wt % and particularly preferred 7 to 15 wt % of partial protein hydrolysate based on dry weight of the total composition.

In a preferred embodiment of the present invention the present enteral composition preferably comprises at most 40 wt %, preferably at most 20 wt % and most preferably at most 15 wt %, preferably 8 to 15 wt %, preferably 8 to 20 wt %, preferably 8 to 40 wt % or preferably 9 to 15 wt %, preferably 9 to 20 wt % or 9 to 40 wt % of partial protein hydrolysate based on dry weight of the total composition.

The partial protein hydrolysate of the present invention may be characterised by at least one of the above-described features or by the cumulative presence of most or all of the above-identified features.

Extensively hydrolysed protein in the present invention relates to protein which has been hydrolysed and has less than 3 wt % of peptides with a size above 5 kDa. Typically, extensively hydrolysed protein has been obtained by protease hydrolysis followed by an ultrafiltration step with by filtrating over a membrane with a cut off of 5 or 3 kDa.

Suitable sources and methods to obtain partial protein hydrolysates are disclosed in example 1, and in WO0141581 p 13 line 13 to p 16, line 1.

In the context of the present invention all relative amounts given in percentage (%) of an indicated overall composition add up to 100% of the indicated overall composition.

In the context of the present invention the wordings "to comprise" and "to contain" and their conjugations are used in one preferred embodiment in their non-limiting sense to mean that items following the wording are included, but items not specifically mentioned are not excluded. In the context of the present invention the wording "to comprise" or "to contain" and their conjugations are used in another preferred embodiment in its limiting sense to mean that items following the wordings are included and items not specifically mentioned are excluded thereby equalling the meaning of the wording "to consist" and its conjugations.

Reference to an element of the present invention, particularly composition or method, by the indefinite article "a" or "an" does not exclude the possibility that more than one of the element is present, unless the context clearly requires that there be one and only one of the elements. The indefinite article "a" or "an" thus usually means "at least one".

Non-Digestible Oligosaccharides of the Present Invention

The present composition comprises non-digestible oligosaccharides. Advantageously and most preferred, the non-digestible oligosaccharide is water-soluble (according to the method disclosed in L. Prosky et al, J. Assoc. Anal. Chem 71: 1017-1023, 1988) and is preferably an oligosaccharide with a degree of polymerisation (DP) of 2 to 200. The average DP of the non-digestible oligosaccharide is preferably below 200, more preferably below 100, even more preferably below 60, most preferably below 40. The non-digestible oligosaccharide is not digested in the intestine by the action of digestive enzymes present in the human upper digestive tract (small intestine and stomach). The non-digestible oligosaccharide is fermented by the human intestinal microbiota. For example, glucose, fructose, galactose, sucrose, lactose, maltose and the maltodextrins are considered digestible. The oligosaccharide raw materials may comprise monosaccharides such as glucose, fructose, fucose, galactose, rhamnose, xylose, glucuronic acid, Gal-Nac etc., but these are not part of the oligosaccharides as in the present invention.

The non-digestible oligosaccharide included in the compositions and methods according to the present invention preferably includes a mixture of non-digestible oligosaccharides. The non-digestible oligosaccharide is preferably selected from the group consisting of fructo-oligosaccharide, such as inulin, non-digestible dextrin, galacto-oligosaccharide, such as transgalacto-oligosaccharide, xylo-oligosaccharide, arabino-oligosaccharide, arabinogalacto-oligosaccharide, gluco-oligosaccharide, such as gentio-oligosaccharide and cyclodextrin, glucomanno-oligosaccharide, galactomanno-oligosaccharide, mannan-oligosaccharide, chito-oligosaccharide, uronic acid oligosaccharide, sialyloligosaccharide, such as 3-SL, 6-SL, LSTa,b,c, DSLNT, S-LNH, DS-LNH, and fuco-oligosaccharide, such as (un)sulphated fucoidan OS, 2-FL, 3-FL, LNFP I, II, III, V, LNnFPI, LNDH, and mixtures thereof, more preferably fructo-oligosaccharide, such as inulin, galacto-oligosaccharide, such as transgalacto-oligosaccharide, which is β linked, uronic acid oligosaccharide and fuco-oligosaccharide and mixtures thereof, even more preferably transgalacto-oligosaccharide, inulin and/or uronic acid oligosaccharides, most preferably transgalacto-oligosaccharide. When the non-digestible oligosaccharide is a mixture, the averages of the respective parameters are used for defining the present invention.

The present invention preferably provides a composition with two different non-digestible oligosaccharides, i.e. non-digestible oligosaccharide A and non-digestible oligosaccharide B. Non-digestible oligosaccharide A and non-digestible oligosaccharide B preferably have a different type of glycosidic linkage, a different degree of polymerisation and/or a different monosaccharide composition.

According to a preferred embodiment of the present invention, the percentage of a particular monosaccharide in non-digestible oligosaccharide A is at least 40 number % higher than the percentage of the same monosaccharide in non-digestible oligosaccharide B, preferably at least 50%, more preferably at least 75%, even more preferably at least 90%. The percentage of a monosaccharide in the non-digestible oligosaccharide can be simply calculated by dividing the number of the respective monosaccharide units, e.g. glucose, in the non-digestible oligosaccharide by the total number of the monosaccharide units in that non-digestible oligosaccharide and multiply it by 100. When the non-digestible oligosaccharide is a non-digestible oligosaccharide mixture, the contribution of each individual monosaccharide unit in the non-digestible oligosaccharide mixture must be taken into account. The percentage of a monosaccharide in a non-digestible oligosaccharide mixture can simply be determined by completely hydrolysing the mixture and determining the number percentage for each monosaccharide. Preferably, non-digestible oligosaccharide A contains at least 40 number % galactose, more preferably at least 67% galactose, more preferably at least 75% galactose. Preferably, non-digestible oligosaccharide B contains at least 30 number % fructose, more preferably at least 67% fructose, even more preferably at least 80% fructose.

According to a preferred embodiment of the present invention, the average DP of non-digestible oligosaccharide A is at least 5 monosaccharide units lower than the average DP of non-digestible oligosaccharide B, preferably at least 10, even more preferably at least 15. Preferably, non-digestible oligosaccharide A has an average DP of 2-10, more preferably 3-5. Preferably non-digestible oligosaccharide B has an average DP below 200, more preferably 11-60, even more preferably 20-30. Including a non-digestible oligosaccharide with an increased degree of polymerisation may be preferred. The non-digestible oligosaccharide A and B with a different DP may have the same or different monosaccharide composition. Preferably, non-digestible oligosaccharide A and B have a different monosaccharide composition and a different DP.

Preferably, at least 80 wt. %, more preferably at least 95 wt. %, most preferably at least 98 wt. % of the cumulative weight of non-digestible oligosaccharide A and B has a DP below 60, more preferably below 40, most preferably below 20. The lower DP advantageously reduces viscosity and increases fermentability of the non-digestible oligosaccharides. Preferably at least 50 wt. %, preferably at least 75 wt. % of the cumulative weight of non-digestible oligosaccharides A and B are non-digestible oligosaccharides with a DP of 2-8. In a further preferred embodiment of the present invention the percentage of at least one glycosidic linkage of non-digestible oligosaccharide A based on total glycosidic linkages of non-digestible oligosaccharide A is at least 40% higher or lower than the percentage of the same glycosidic linkage in oligosaccharide B, preferably at least 50%, even more preferably at least 75%. The term "glycosidic linkage" as used in the present invention refers to a C—O—C linkage formed between the rings of two cyclic monosaccharides by the elimination of water. An increased diversity in glycosidic linkages is preferred. Glycosidic linkages differ in that they covalently bind carbon atoms in the monosaccharide units at differently numbered positions, and/or that they form α or β bonds. Examples of different glycosidic linkages occurring in non-digestible saccharides are β(1,3), α(1,4), β(2,1), α(1,2), and β(1,4) linkages. Preferably the glycosidic linkages in non-digestible oligosaccharide A comprises at least 40% β(1,4) and/or β(1,6) glycosidic linkages, more preferably at least 75%. The glycosidic linkages in non-digestible oligosaccharide B preferably comprise at least 40% β(2,1) glycosidic linkages, more preferably at least 75%. Preferably, non-digestible oligosaccharide A and B differ in monosaccharide unit composition and in type of glycosidic linkage. Preferably, non-digestible oligosaccharide A and B differ in type of glycosidic linkage and DP. Most preferably, non-digestible oligosaccharide A and B differ in type of glycosidic linkage, monosaccharide composition and DP.

Preferably, at least 60%, more preferably at least 75% even more preferably 90%, most preferably 98% of the total monosaccharide units of the non-digestible oligosaccharide, in particular non-digestible oligosaccharide A and B, are monosaccharides selected from the group consisting of galactose (gal), fructose (fru) and glucose (glu) monosaccharides.

Non-digestible oligosaccharide A is preferably an oligosaccharide selected from the group consisting of β-galacto-oligosaccharide, α-galacto-oligosaccharide, and galactan. According to a more preferred embodiment non-digestible oligosaccharide A is β-galacto-oligosaccharide. β-galacto-oligosaccharide is also sometimes referred to as transgalacto-oligosaccharide. Preferably non-digestible oligosaccharide A comprises galacto-oligosaccharides with β(1,4), β(1,3) and/or β(1,6) glycosidic bonds and a terminal glucose. Transgalacto-oligosaccharide is for example available under the trade name Vivinal®GOS (Borculo Domo Ingredients, Zwolle, Netherlands), Bi2muno (Clasado), Cup-oligo (Nissin Sugar) and Oligomate55 (Yakult).

Non-digestible oligosaccharide B is preferably fructo-oligosaccharide. A fructo-oligosaccharide may in other context have names like fructopolysaccharides, oligofructose, polyfructose, polyfructan, inulin, levan and fructan and may refer to oligosaccharides comprising β-linked fructose units, which are preferably linked by β(2,1) and/or β(2,6) glycosidic linkages, and a preferable DP between 2 and 200. Preferably, the fructo-oligosaccharide contains a terminal β(2,1) glycosidic linked glucose. Preferably, the fructo-oligosaccharide contains at least 7 β-linked fructose units. In a further preferred embodiment inulin is used as non-digestible oligosaccharide B. Inulin is a type of fructo-oligosaccharide wherein at least 75% of the glycosidic linkages are β(2,1) linkages. Typically, inulin has an average chain length between 8 and 60 monosaccharide units. A suitable fructo-oligosaccharide for use in the compositions of the present invention is commercially available under the trade name Raftiline®HP (Orafti). Other suitable sources are raftilose (Orafti), fibrulose and fibruline (Cosucra) and Frutafit and frutalose (Sensus).

Most preferred is transgalacto-oligosaccharide with an average DP below 10, preferably below 6 as non-digestible oligosaccharide A and a fructo-oligosaccharide with an average DP above 7, preferably above 11, even more preferably above 20, as non-digestible oligosaccharide B.

If the present enteral composition comprises non-digestible oligosaccharide A and B, the weight ratio non-digestible oligosaccharide A to non-digestible oligosaccharide B is preferably from 1/99 to 99/1, more preferably from 1/19 to 19/1, even more preferably from 1 to 19/1. This weight ratio is particularly advantageous when non-digestible oligosaccharide A has a low DP and non-digestible oligosaccharide B has a relatively high DP. Preferably oligosaccharide A is a transgalacto-oligosaccharide and oligosaccharide B is a fructo-oligosaccharide Thus, according to one embodiment of the present invention the composition comprises the non-digestible oligosaccharides A and B, wherein the non-digestible oligosaccharides A and B differ either:
i) in the percentage of at least one monosaccharide of oligosaccharide A based on total monosaccharide units of oligosaccharide A, the monosaccharide being at least 40 number % higher that the percentage of the same monosaccharide in oligosaccharide B; and/or
ii) in the percentage of at least one glycosidic linkage of oligosaccharide A based on total glycosidic linkages of oligosaccharide A, the glycosidic linkage being at least 40% higher than the percentage of the same glycosidic linkage in oligosaccharide B; and/or
iii) in the degree of polymerisation of oligosaccharide A, degree of polymerisation of oligosaccharide A being at least 5 monosaccharide units lower than the degree of polymerisation of oligosaccharide B.

In a more preferred embodiment the present composition further comprises a non-digestible oligosaccharide C. The non-digestible oligosaccharide C comprises uronic acid oligosaccharides. The term uronic acid oligosaccharide as used in the present invention refers to an oligosaccharide wherein at least 50 number % of the monosaccharide units present in the oligosaccharide is one selected from the group consisting of guluronic acid, mannuronic acid, galacturonic acid, iduronic acid, riburonic acid and glucuronic acid. In a preferred embodiment the uronic acid oligosaccharide comprises at least 50 number % galacturonic acid based on total uronic acid units in the uronic acid oligosaccharide. The uronic acid oligosaccharides used in the invention are preferably prepared from degradation of pectin, pectate, alginate, chondroitine, hyaluronic acids, heparine, heparane, bacterial carbohydrates, and/or sialoglycans, more preferably of pectin and/or alginate, even more preferably of pectin, most preferably polygalacturonic acid. Preferably the degraded pectin is prepared by hydrolysis and/or beta-elimination of fruit and/or vegetable pectins, more preferably apple, citrus and/or sugar beet pectin, even more preferably apple, citrus and/or sugar beet pectin degraded by at least one lyase. Preferably, the non-digestible oligosaccharide is galacturonic acid oligosaccharide.

Preferably, the present composition comprises between 25 and 100 wt. %, more preferably between 50 and 100 wt. % uronic acid oligosaccharide with a DP of 2 to 250 based on total weight of uronic acid oligosaccharide in the composition, more preferably a DP of 2 to 100, even more preferably a DP of 2 to 50, most preferably a DP of 2 to 20 based on total weight of uronic acid oligosaccharide in the composition.

In a preferred embodiment, at least one of the terminal hexuronic acid units of the uronic acid oligosaccharide has a double bond. The double bond effectively protects against attachment of pathogenic bacteria to intestinal epithelial cells. This is advantageous for infants. Preferably, one of the terminal hexuronic acid units comprises the C4-C5 double bond. The double bond at terminal hexuronic acid unit can for example be obtained by enzymatic hydrolysis of pectin with lyase.

The uronic acid oligosaccharide can be derivatised. The uronic acid oligosaccharide may be methoxylated and/or amidated. In one embodiment the uronic acid oligosaccharides are characterized by a degree of methoxylation above 20%, preferably above 50% even more preferably above 70%. As used herein, "degree of methoxylation" (also referred to as DE or "degree of esterification") is intended to mean the extent to which free carboxylic acid groups contained in the uronic acid oligosaccharide have been esterified, e.g. by methylation.

Preferably, the present enteral composition comprises the non-digestible oligosaccharides transgalacto-oligosaccharide, fructo-oligosaccharide and a pectin degradation product.

The weight ratio transgalacto-oligosaccharide:fructo-oligosaccharide:pectin degradation product is preferably (20 to 2):1:(1 to 3), more preferably (12 to 7):1:(1 to 2).

Preferably, the present invention relates to an enteral composition, wherein the non-digestible oligosaccharide is selected from the group consisting of fructo-oligosaccharide, galacto-oligosaccharide and uronic acid oligosaccharide, wherein the uronic acid oligosaccharide is preferably galacturonic acid oligosaccharide.

The present enteral composition preferably comprises 0.05 to 20 wt. % total non-digestible oligosaccharide, more preferably 0.5 to 15 wt. %, even more preferably 1 to 10 wt. %, most preferably 2.0 to 10 wt. %, based on dry weight of the present composition.

Based on 100 ml the present enteral composition preferably comprises 0.01 to 2.5 wt. % total non-digestible oligosaccharide, more preferably 0.05 to 1.5 wt. %, even more preferably 0.25 to 1.5 wt. %, based on 100 ml of the present composition.

Enteral Composition

The present invention relates to non-digestible oligosaccharides for use in the enhancement of a partial protein hydrolysate-induced oral tolerance against dietary proteins, the partial protein hydrolysate being characterised in that it comprises at least 3 wt % of peptides with a size of 5 kDa or above and at least 50 wt. % of peptides with a size below 5 kDa, preferably in an enteral composition of the present invention.

The present invention relates to non-digestible oligosaccharides for use in the enhancement of a primary allergy preventing effect of a partial protein hydrolysate against dietary proteins, the partial protein hydrolysate being characterised in that it comprises at least 3 wt % of peptides with a size kDa or above and at least 50 wt. % of peptides with a size below 5 kDa, preferably in an enteral composition of the present invention.

The present invention relates to an enteral composition, comprising non-digestible oligosaccharides and at least one partial protein hydrolysate, preferably according to the present invention, wherein the partial protein hydrolysate is a partial whey protein hydrolysate and wherein the non-digestible oligosaccharide is a mixture of galacto-oligosaccharides, fructo-oligosaccharides and galacturonic acid oligosaccharides. Preferably, the partial protein hydrolysate of the enteral composition is characterised in that it comprises at least 3 wt % of peptides with a size of 5 kDa or above and at least 50 wt. % of peptides with a size below 5 kDa.

An enteral composition of the present invention is preferably a nutritional composition. Preferably, the enteral composition is for oral administration.

The enteral composition of the present invention comprises, as explained above, a partial protein hydrolysate and a non-digestible oligosaccharide.

In a preferred embodiment, the enteral composition of the present invention comprises a) at least 5 wt. % partial whey protein hydrolysate or at least 5 wt.-% of the at least one beta-lactoglobulin peptide, each based on dry weight of the composition, and b) at least 1 wt % of the sum of galacto-oligosaccharides, fructo-oligosaccharides and galacturonic acid oligosaccharides, based on dry weight of the composition, wherein, preferably, the weight ratio of galacto-oligosaccharides:fructo-oligosaccharides: galacturonic acid oligosaccharides is (20-4):(0.5-2):1.

In addition, the enteral composition of the present invention may further comprise a lipid (also termed lipid component), in particular fat.

The present enteral composition preferably comprises as lipids vegetable lipids and/or marine oils, such as algae oils, bacterial oils, animal oils, vegetable oils or fish oils.

The present enteral composition may in a further preferred embodiment also comprises in addition to the non-digestible oligosaccharide a further carbohydrate component, such as digestible carbohydrates, preferably lactose.

In a further preferred embodiment of the present invention the enteral composition comprises in addition to the partial protein hydrolysate a further protein component such as non-hydrolysed protein or, preferably, an extensive protein hydrolysate.

In a further preferred embodiment of the present invention the enteral composition comprises in addition to the beta-lactoglobulin peptide a further protein component such as non-hydrolysed protein or, preferably, an extensive protein hydrolysate or free amino acids. Preferably, the extensive protein hydrolysate has a free amino acid content of above 10 g per 100 g protein. Preferably, the term protein as used here includes peptides and free amino acids.

In a further preferred embodiment the present invention relates to an enteral composition comprising at least one non-digestible oligosaccharide and at least one partial protein hydrolysate for use in the induction of oral tolerance against dietary proteins, the partial protein hydrolysate being characterized in that it comprises at least 3 wt. % of peptides with a size of 5 kDa or above and at least 50 wt. % of peptides with a size below 5 kDa, and which enteral composition comprises at least one beta-lactoglobulin peptide comprising a sequence selected from the group consisting of SEQ ID NO 1, SEQ ID NO 2, SEQ ID NO 3 and SEQ ID NO 4. Preferably, the beta-lactoglobulin peptide has a size of below 5 kDa.

In a further preferred embodiment the present invention relates to an enteral composition comprising at least one non-digestible oligosaccharide and at least one partial protein hydrolysate for use in the prevention of food allergy or inflammatory bowel disease, the partial protein hydrolysate being characterized in that it comprises at least 3 wt. % of peptides with a size of 5 kDa or above and at least 50 wt. % of peptides with a size below 5 kDa, and which enteral composition comprises at least one beta-lactoglobulin peptide comprising a sequence selected from the group consisting of SEQ ID NO 1, SEQ ID NO 2, SEQ ID NO 3 and SEQ ID NO 4. Preferably, the beta-lactoglobulin peptide has a size of below 5 kDa.

Thus, in a preferred embodiment of the present invention the enteral composition of the present invention comprises a protein component, including the partial protein hydrolysate, a carbohydrate component, including the non-digestible oligosaccharide, a lipid component and optionally a liquid solvent such as water.

The present composition preferably contains at least 50 wt. % protein component derived from non-human milk, more preferably at least 90 wt. %, each based on dry weight of total protein. Preferably, the present composition contains at least 50 wt. % cow's milk derived protein, more preferably at least 90 wt. %, each based on dry weight of total protein. Preferably, the present composition comprises protein derived from acid whey and/or sweet whey with a reduced concentration of glycomacropeptide. Typically, glycomacropeptide (GMP) with a molecular weight of 8000 daltons is a casein-derived whey protein containing amino acid residues 106-169 of kappa-casein, and is released from kappa-casein by the proteolytic action of rennin (chymosin). Preferably, the present enteral composition comprises protein derived from β-casein, beta-lactoglobulin and/or α-lactalbumin. In another embodiment of the present invention, the protein is pea, soy and/or rice protein.

Preferably, the present enteral composition comprises partial whey protein hydrolysate and partial casein hydrolysate. Partial casein hydrolysate and partial whey protein hydrolysate are preferably present in a weight ratio casein:whey of 10:90 to 90:10, more preferably 20:80 to 80:20.

The present enteral composition preferably includes both casein hydrolysate and whey protein hydrolysate because the amino acid composition of bovine casein is more similar to the amino acid composition found in human milk protein and whey protein is easier to digest and found in greater ratios in human milk.

The present enteral composition preferably contains 5 to 25%, preferably 7 to 25%, preferably 5 to 20%, preferably 5 to 16%, preferably 5 to 12% protein based on total calories, most preferably 7.0 to 12.0% protein based on total calories of the composition. The total caloric value can be calculated based on the amount of digestible carbohydrates, fat and protein.

Based on 100 ml the present enteral composition preferably comprises 0.5 to 2.5 wt. % protein, more preferably 0.05 to 1.5 wt. %, even more preferably 1 to 3 wt. %, based on 100 ml of the present composition.

The term protein as used in the present invention refers to the sum of proteins, peptides and free amino acids.

The present enteral composition preferably contains 0.5 to 6.0 g, more preferably 1.0 to 3.0 g, even more preferably 1.0 to 2.5 g of protein per 100 ml of the ready to feed composition.

The present enteral composition preferably comprises at least 7.0 wt. %, more preferably at least 8.0 wt. %, most preferably at least 9 or at least 10 wt % protein based on dry weight of the total composition.

Preferably, the present enteral composition comprises at most 40 wt. %, more preferable at most 15 wt %, preferably at most 20 wt. % of protein based on dry weight of the total composition.

The wt. % protein based on dry weight of the present enteral composition is calculated according to the Kjeldahl-method by measuring total nitrogen and using a conversion factor of 6.38, preferably in case of casein, or a conversion factor of 6.25 for other proteins than casein.

The present enteral composition preferably contains at least 50 wt. %, preferably at least 80 wt. %, particularly at least 90 wt %, most preferably 100 wt. % of the partial protein hydrolysate of the present invention, based on dry weight of the total protein in the present enteral composition.

The present enteral composition preferably contains less than 10 g free amino acids per 100 g protein, more preferably less than 7 g. A relatively low amino acid content results in a low osmolarity and thus prevents disturbances of the gastrointestinal tract/digestive system such as diarrhoea. A low content of free amino acids is of further importance for reducing the bitter taste; free amino acids give the formula a bitter taste. Furthermore, free amino acids are absorbed worse in the intestinal tract compared to peptides. Therefore, the amount of free amino acids in the present enteral composition is preferably limited.

The present enteral composition preferably also comprises a lipid component, preferably a fat, and a protein component and preferably a digestible carbohydrate component, wherein the lipid component preferably provides 30 to 60% of total calories, the protein component preferably provides 5 to 20%, more preferably 5 to 15%, of the total calories and the digestible carbohydrate component preferably provides 25 to 75% of the total calories. Preferably, the present composition comprises a lipid component providing 35 to 50% of the total calories, a protein component provides 6 to 12% of the total calories and a digestible carbohydrate component provides 40 to 60% of the total calories. The amount of total calories is determined by the sum of calories derived from protein, lipids and digestible carbohydrates.

The present composition is not human breast milk. Preferably, the present enteral composition is free of living or dead probiotics, in particular bifidobacteriae or lactobacillae. Preferably, the present enteral composition is free of growth factors and/or cytokines. Preferably, the present enteral composition is free of TGF, particularly TGF-beta.

The compositions of the invention preferably comprise other components, such as vitamins and/or minerals, preferably according to international directives for infant formulae.

In one embodiment the present enteral composition is in dry form, for instance is a powder suitable for making a liquid composition after reconstitution with an aqueous solution, preferably with water. Preferably, the enteral composition is a powder, preferably to be reconstituted with water.

In order to meet the caloric requirements of the infant, the present enteral composition preferably comprises 50 to 200 kcal/100 ml liquid, more preferably 60 to 90 kcal/100 ml liquid, even more preferably 60 to 75 kcal/100 ml liquid. This caloric density ensures an optimal ratio between water and calorie consumption. The osmolarity of the present composition is preferably between 150 and 420 mOsmol/l, more preferably 260 to 320 mOsmol/l. The low osmolarity aims to reduce the gastrointestinal stress. Stress can induce adipocyte formation.

Preferably, the present enteral composition is in a liquid form, preferably with a viscosity below 35 mPa·s, more preferably below 6 mPa·s as measured in a Brookfield viscometer at 20° C. at a shear rate of 100 s$^{-1}$. Suitably, the present enteral composition is in a powdered from, which preferably can be reconstituted with water to form a liquid, or in a liquid concentrate form, which should be diluted with water. When the present enteral composition is in a liquid form, the preferred volume administered on a daily basis is in the range of about 80 to 2500 ml, more preferably about 450 to 1000 ml per day.

Use

The present enteral composition of the present invention is preferably for use in infants, i.e. is an infant nutritional composition. Hence the present enteral composition is preferably administered to the human subject during the first 3 years of life. Preferably, the present composition is an infant formula or a follow-on-formula, or a toddler milk, that means for humans elder than infants.

In one embodiment of the use according to the present invention, the enteral, preferably nutritional, composition is for feeding or is used for feeding a human subject with an age from 0 to 36 months. The present enteral composition is advantageously administered to a human of 0 to 24 months, more preferably to a human of 0 to 18 months, most preferably to a human of 0 to 12 months.

Preferably, the present enteral composition is for use in the prevention of food allergy.

Preferably, the present enteral, preferably nutritional, composition is for providing the daily nutritional requirements to a human, in particular for administration to, in particular for feeding, humans, in particular infants including toddlers, preferably at risk for developing an allergy, in particular for developing allergic symptoms.

In the present invention, the term tolerance is to be understood as a state of specific immunological unresponsiveness. Both humoral (antibodies) and cell mediated (lymphocyte) pathways of the immune response may be suppressed by tolerance induction. A breakdown of oral tolerance is considered to be the underlying cause of food allergy. Oral immune tolerance means the specific suppression of cellular and/or humoral immune reactivity to an antigen by prior administration of the antigen by the oral route. It probably evolved to prevent hypersensitivity reactions to food proteins. It is of immense immunological importance, since it is a continuous natural immunologic event driven by exogenous antigen. Due to their privileged access to the internal milieu, antigens that continuously contact the mucosa represent a frontier between foreign and self components. Oral immune tolerance evolved to treat external agents that gain access to the body via a natural route as internal components without danger signals, which then become part of self. Failure of oral immune tolerance is attributed to the development and pathogenesis of several immunologically based diseases, including food allergy and inflammatory bowel disease, particularly Crohn's disease and ulcerative colitis.

In the present invention the tolerance is induced or acquired, wherein tolerance to external antigens can be created by manipulating the immune system. Acquired or induced tolerance refers to the immune system's adaptation to external antigens characterized by a specific non-reactivity of the lymphoid tissues to a given antigen that in other circumstances would likely induce cell-mediated or humoral immunity.

The present enteral composition is preferably for use in the induction of oral tolerance, preferably for use in the induction of immune tolerance, most preferably for use in the induction of oral immune tolerance, preferably in humans, in particular infants.

Thus, in a preferred embodiment of the present invention the present enteral compositions for use in inducing oral tolerance are particularly useful for preventing, preferably primarily preventing, food allergy, preferably cow milk allergy and/or the development of atopic diseases, such as atopic eczema, allergic rhinitis, atopic dermatitis or asthma.

The present enteral composition is preferably for use in the induction of tolerance, preferably in the oral tolerance in humans, in particular infants at risk of developing an allergy, in particular a food allergy, in particular symptoms of a food allergy.

In a furthermore preferred embodiment the present enteral composition is a hypoallergenic enteral composition.

In a furthermore preferred embodiment of the present invention the present enteral composition is preferably for use in the prevention or treatment of inflammatory bowel disease.

All compositions and substances identified herein to be suitable and designed for a use according to the present invention are to be understood also to be suitable and designed for being applied in methods of treatment or methods for feeding a subject, in particular a human subject, in need thereof Further preferred embodiments are the subject matter of the subclaims.

The invention will be further described by way of the non-limiting examples.

EXAMPLE 1

Non-digestible oligosaccharides synergistically potentiates the capacity of partially hydrolysed protein to induce oral tolerance to protein in a mouse model of protein allergy.

Whey was obtained from DMV International, Veghel, the Netherlands. A partial whey hydrolysate (pWH) was manufactured at Danone Research Centre for Specialised Nutrition by enzymatic hydrolysis under the following specified conditions.

19.5 kg of demineralised water (in the following "demi water") of 12° C. was put into a bin and mixed with 4.1 kg demineralised whey (Deminal, Friesland Foods Domo) and 1.41 kg of lactalis Nutriwhey800 (DMV Campina) for 30 minutes.

The solution was given a heat treatment of 2 minutes at 78° C. The product was cooled to 60° C. after the heat treatment.

15.6 g $Ca(OH)_2$, 1.84 g $Mg(OH)_2$, 16.1 g KOH and 15.25 g NaOH was dissolved in 235 ml demi water to obtain a base solution. The hydrolysis tank was filled with 12 kg of the heat treated whey solution and stirred. The temperature was kept at 58° C. The base solution was used to adjust the pH of the hydrolysis tank to pH of 7.75.

16.8 g Alcalase and 3.8 g Flavourzyme was mixed and added to the fermentor quickly. The base solution was used to regulate the pH at 7.75. The hydrolysis took place for 180 minutes.

The enzymatic process was stopped by fast cooling and the solution was freezed. The pWH was further characterized by analysis of the peptide by means of size exclusion high pressure liquid chromatography.

The size distribution was as follows: 85 wt. %<1 kD, 8 wt. % 1 to <2 kDa, 4 wt. % 2 to <5 kDa, 1 wt. % 5 to <10 kDa, 0.6 wt. % 10 to 20 kDa and 1.4 wt. %>20 kDa.

Three- to 4-week-old pathogen free female C3H/HeOuJ mice were purchased from Charles River Laboratories (Maastricht, the Netherlands), maintained on cow's milk protein free standard mouse chow (AIN-93G soy, Special Diets Services, Witham, Essex, UK).

Mice were fed a control diet (table 1, below) and sensitized orally, using a blunt needle, on day 0, 7, 14, 21 and 28 with 20 mg whey protein per animal homogenized in PBS (0.5 ml, Cambrex Bio Science, Verviers, Belgium) mixed with 10 μg cholera toxin (Quadratech Diagnostics, Epsom, UK) as an adjuvant. Non-sensitized mice received cholera toxin only. Prior to whey protein sensitization mice where pre-treated orally (daily; day −7 until day −2) with PBS as a control or 50 mg pWH. To investigate the effect of a diet comprising non-digestible oligosaccharides diet on oral tolerance induction by pWH mice were fed a diet (AING-93G soy containing 2 wt. % of the sum of trans-galacto-oligosaccharides (source Vivinal-GOS), long chain fructo-oligosaccharides (FOS, source RaftilinHP) and galacturonic acid oligosaccharides (AOS, pectin lysate) (table 1, below).

TABLE 1

| | | |
|---|---|---|
| Diet of mice | | |
| g/10 kg chow | diet # P1 (control) | diet # P2 (GFA) |
| Carbohydrates | | |
| cornstarch | 4769,820 | 4719,708 |
| dextrinized cornstarch | 1549,488 | 1549,488 |
| sucrose | 1163,892 | 1163,892 |
| fiber source (cellulose) | 600,000 | 480,000 |
| lactose | 36,108 | |
| glucose | 34,512 | |
| GOS/FOS | | 216,000 |
| AOS | | 24,000 |

TABLE 1-continued

Diet of mice

| g/10 kg chow | diet # P1 (control) | diet # P2 (GFA) |
|---|---|---|
| Protein | | |
| soy bean protein | 2400,000 | 2400,000 |
| L-cysteine | 36,000 | 36,000 |
| Fat | | |
| soybean oil | 840,000 | 840,000 |
| Others | | |
| Mineral mix | 420,000 | 420,000 |
| Vitamin mix | 120,000 | 120,000 |
| Choline bitartrate | 30,000 | 30,000 |
| TBHQ | 0,168 | 0,168 |
| Raw materials | | |
| Total carbohydrates | 8154 | 8153 |
| Total protein | 2436 | 2436 |
| Total Fat | 840 | 840 |
| Total Others | 570 | 570 |
| Total diet | 12000 | 11999 |

Trans-galacto-oligosaccharides, long chain fructo-oligosaccharides RaftilinHP and galacturonic acid oligosaccharides were present in a 9:1:1 wt. ratio in the diet (AIN-93G soy, Special Diets Services, Witham, Essex, UK) from day −7 till day −2 in combinations with or without a pWH pretreatment prior to whey-protein sensitization.

One week after the last sensitization the acute allergic skin response (ear swelling at 1 hour) after intradermal whey protein challenge was measured. An acute allergen specific ear swelling in whey sensitized mice was determined at 1 hour after intradermal challenge with 10 μg whey protein in the ear pinnae. As a negative control non-sensitized mice were challenged in the ear with whey protein. Ear thickness was measured in duplicate using a digital micrometer (Mitutoyo, Veenendaal, the Netherlands). The allergen-specific net ear swelling was calculated by correcting the allergen-induced increase in ear thickness with the non-specific ear swelling due to local injection in the non-sensitized mice. The ear swelling is expressed as delta μm.

Results:

The results are shown in table 2. Intradermal ear challenge with whey induced a significant ear swelling at 1 hour in whey sensitized animals compared to non-sensitized mice (120.9±12.4 μm vs 25.42±6.8 μm; p<0.01). Pretreatment with the pWH with limited sensitizing capacities significantly reduced the acute ear swelling response (83.58±5.6 μm). Feeding the mice for 5 days with the non-digestible oligosaccharide (NDO) mixture before sensitization did not significantly affect the acute allergic skin response to whey protein compared to control diet (112.1±8.8 μm). Interestingly, the acute skin response completely abolished in the pWH pre-treated mice fed the diet comprising also non-digestible oligosaccharides (22.08±6.3 μm). This effect was synergistic, being much higher than expected based on the added effects based on pWH or NDO alone.

TABLE 2

Effect of oral pretreatment with partially hydrolysed whey protein (pWH), non-digestible oligosaccharides (NDO), or both on allergic reaction to whey protein measured as immediate type hyperresponsiveness (ITH) ear swelling.

| Mice treatment group | ΔITH μm ± S.E. | Relative ITH | Relative tolerance |
|---|---|---|---|
| Non sensitized control | 25.42 ± 6.8 | 0% | 100% |
| No pretreatment | 120.9 ± 12.4 | 100% | 0% |
| eWH pretreatment | 134.6 ± 12.6 | >100% | 0% |
| whey protein pretreatment | 54.33* ± 6.1 | 30% | 70% |
| pWH pre-treatment (basic value) | 83.58* ± 5.6 | 61% | 39% |
| NDO pretreatment | 112.1 ± 8.8 | 91% | 9% |
| pWH + NDO pretreatment | 22.08* ± 6.3 | 0% | 100% |

* $P < 0.05$ compared to non-pretreated group.

EXAMPLE 2

Infant milk formula with partially hydrolyzed whey, GOS (galacto oligosaccharide), FOS (fructo oligosaccharide), AOS (acid oligosaccharide, i. e. galacturonic acid oligosaccharide) comprising per 100 ml ready to drink:

66 kcal 1.5 g protein equivalent (partially hydrolysed whey protein as in example 1, Kjeldahl factor 6.25 used)

7.2 g digestible carbohydrates (mainly lactose)

3.4 g fat (vegetable fats, fish oil)

0.8 g non-digestible oligosaccharides 0.612 g Galacto-oligosaccharides 0.068 g Long chain fructo-oligosaccharides 0.12 g Pectin lysate (AOS)

Minerals, trace elements vitamins and other micronutrients according to international guidelines for infant formulas are contained as well.

EXAMPLE 3

The experiment of example 1 was repeated, except that an extra group was included wherein in the group pretreated with eWH also received a diet with the NDO during the pretreatment. The results are shown in table 3 below and confirm the experiment shown in example 1 again showing the highest tolerance induction with a pretreatment with pWH and NDO. These experiments further show that the oral tolerance inducing effect cannot be obtained using a pretreatment with eWH+NDO.

TABLE 3

Effect of oral pretreatment with partially hydrolysed whey protein (pWH), non-digestible oligosaccharides (NDO), or both or extensively hydrolysed whey protein (eWH) or intact whey protein pretreatment on allergic reaction to whey protein measured as immediate type hyperresponsiveness (ITH) ear swelling

| Mice treatment group | ΔITH μm ± S.E. | Relative ITH | Relative tolerance |
|---|---|---|---|
| Non sensitized control | 36.7 ± 5.7 | 0% | 100% |
| No pre-treatment | 121.1 ± 18.9 | 100% | 0% |
| eWH pre-treatment | 88.79 ± 6.8 | 62% | 38% |
| whey protein pretreatment | 39.25* ± 5.3 | 3% | 97% |
| pWH pretreatment (basic value) | 67.15* ± 10.7 | 36% | 64% |

TABLE 3-continued

Effect of oral pretreatment with partially hydrolysed whey protein (pWH), non-digestible oligosaccharides (NDO), or both or extensively hydrolysed whey protein (eWH) or intact whey protein pretreatment on allergic reaction to whey protein measured as immediate type hyperresponsiveness (ITH) ear swelling

| Mice treatment group | ΔITH μm ± S.E. | Relative ITH | Relative tolerance |
|---|---|---|---|
| NDO pre-treatment | 109.1 ± 13.1 | 86% | 14% |
| pWH + NDO pretreatment | 32.58* ± 8.1 | 0% | 100% |
| eWH + NDO pretreatment | 114.5 ± 14.4 | 92% | 8% |

\* $P < 0.05$ compared to non-pretreated group.
\*\* $P < 0.01$ compared to non-pretreated group.

EXAMPLE 4

Non-digestible oligosaccharides synergistically potentiate the capacity of specific whey protein peptides to induce oral tolerance to protein in a mouse model of protein allergy.

Peptides were synthesized and prescreened with an assay with T cell lines. Twenty-five 18-amino-acid-long synthetic peptides with 12 amino-acid overlap spanning the B variant of β-LG and six synthetic peptides of the A variant of β-LG were obtained from JPT Peptide Technologies (Berlin, Germany).

Epstein Barr Virus (EBV)-transformed B cells were cultured in RPMI 1640-GlutaMAX™-I supplemented with 10% heat-inactivated FBS and 2% Pen/Strep. Cow's milk-specific T cell lines (TCL) were generated as described previously by Schade et al 2000, J Allerg. Clin. Immunol. 106: 1155-62. The TCLs were cultured in Yssel's medium containing 2% HS, 2% Pen/Strep, 1% Glut, 50 IU/ml IL-2 and 50 IU/ml IL-4 and were re-stimulated every two weeks with cow's milk to maintain them in culture. For the re-stimulation, autologous EBV-transformed B cells were pre-incubated overnight with 50 μg/ml cow's milk protein mixture. Subsequently, the B cells were irradiated and added to the TCLs.

Peptide-specific T cell proliferation was tested as described before by Ruiter et al, 2006, Clin Exp Allergy 36:303-10. In short, irradiated EBV-transformed B cells ($4 \times 10^4$/well) were pre-incubated overnight in triplicate in 96-well U-plates with 50 μg/ml major allergen or 10 μg/ml synthetic peptide (either a mixture of 2 or 3 peptides, or single peptides). Whey protein (prolacta) was obtained from Lactalis, Laval, France). Caseinate was purchased from FrieslandCampina Domo (Amersfoort, The Netherlands). For the cow's milk protein mixture, prolacta and cacaseinate were mixed in a 1:1 ratio. Also iα-lactalbumin (α-LAC) and β-lactoglobulin (β-LG) were tested as controls. Subsequently, $4 \times 10^4$ T cells were added to the wells and cultured for 24 hours. The next day, tritiated thymidine (1 μCi/well) was added. After 18 hours, the cells were harvested on glass fibre filters and the [$^3$H]-TdR incorporation was measured using a Microbeta2 plate counter (Perkin Elmer, Waltham, Mass., USA). The incorporation was expressed as counts per minute (cpm) and background proliferation of EBV B cells was subtracted. All tests were performed in Yssel's medium with 2% Pen/Strep and 1% Glut and incubations were done at 37° C. in a humidified 5% $CO_2$ atmosphere. Each TCL was tested at least three times.

The peptides having the highest T cell reactivity were selected for further testing in an animal model. These nine peptides were derived from beta-lactoglobulin.

Three- to four-week-old pathogen free female C3H/HeOuJ mice (Charles River Laboratories, Maastricht, The Netherlands) were used for this experiment. The mice were maintained on cow's milk protein free standard mouse chow (AIN-93G soy, Special Diets Services, Wijk bij Duurstede, the Netherlands).

The AIN-93G control diet was mixed with non-digestible oligosaccharides (2% w/w). The same non-digestible oligosaccharides were used as in example 1.

18-amino-acid-long synthetic peptides of beta-lactoglobulin were obtained from JPT Peptide Technologies (Berlin, Germany) (Table 4). Whey protein was purchased from DMV International (Veghel, The Netherlands). Cholera toxin (CT) was obtained from Quadratech Diagnostics (Epsom, United Kingdom). Phosphate-buffered saline (PBS) was obtained from Cambrex Bio Science (Verviers, Belgium).

TABLE 4

Sequence information of the peptides

| Peptide | Sequence | Amino acids (AA) beta-lactoglobulin |
|---|---|---|
| 1 | Gln Lys Val Ala Gly Thr Trp Tyr Ser Leu Ala Met Ala Ala Ser Asp Ile Ser (SEQ ID NO 1) | AA 13-30 |
| 2 | Trp Tyr Ser Leu Ala Met Ala Ala Ser Asp Ile Ser Leu Leu Asp Ala Gln Ser (SEQ ID NO 2) | AA 19-36 |
| 3 | Ala Ala Ser Asp Ile Ser Leu Leu Asp Ala Gln Ser Ala Pro Leu Arg Val Tyr (SEQ ID NO 3) | AA 25-42 |
| 4 | Leu Leu Asp Ala Gln Ser Ala Pro Leu Arg Val Tyr Val Glu Glu Leu Lys Pro (SEQ ID NO 4) | AA 31-48 |
| 5 | Lys Val Leu Val Leu Asp Thr Asp Tyr Lys Lys Tyr Leu Leu Phe Cys Met Glu (SEQ ID NO 5) | AA 91-108 |
| 6 | Thr Asp Tyr Lys Lys Tyr Leu Leu Phe Cys Met Glu Asn Ser Ala Glu Pro Glu (SEQ ID NO 6) | AA 97-114 |
| 7 | Leu Leu Phe Cys Met Glu Asn Ser Ala Glu Pro Glu Gln Ser Leu Ala Cys Gln (SEQ ID NO 7) | AA 103-120 |
| 8 | Ala Leu Lys Ala Leu Pro Met His Ile Arg Leu Ser Phe Asn Pro Thr Gln Leu (SEQ ID NO 8) | AA 139-156 |
| 9 | Met His Ile Arg Leu Ser Phe Asn Pro Thr Gln Leu Glu Glu Gln Cys His Ile (SEQ ID NO 9) | AA 145-162 |

Shortly prior to the experiment, the peptides were suspended in PBS. The peptides were combined in three mixtures, namely peptides 1-4 in mixture 1, peptides 5-7 in mixture 2 and peptides 8 and 9 in mixture 3. The final concentration of each peptide in the mixture was 8 mg/ml. The mice (n=6 per group) were treated orally using a blunt needle with 0.5 ml of the peptide mixtures or PBS in the week prior to the sensitization (from day −7 until day −2). During this week (day −7 until day 0) the mice received either the standard AIN-93G (control) diet or the prebiotic diet. After this week all mice received the control diet. On day 0, 7, 14, 21 and 28, the mice were orally sensitized with 20 mg whey and 10 μg CT in 0.5 ml PBS. The non-sensitized mice were treated with 10 µg CT in 0.5 ml PBS. Five days after the last sensitization, the mice received an intradermal challenge in the ear pinnae with 10 µg whey in 20 µl PBS. Before and 1 h after the challenge, the ear thickness was measured using a digital micrometer (Mitutoyo, Veenendaal, the Netherlands). The difference in the ear thickness (ear swelling) is an indication for the acute allergic response and is expressed as delta µm.

Results are shown in Table 5.

TABLE 5

Effect of oral pretreatment with peptide mixtures, non-digestible oligosaccharides (NDO), or both on allergic reaction to whey protein measured as immediate type hyperresponsiveness (ITH) ear swelling.

| Mice treatment group | ΔITH µm ± S.E. | Relative ITH | Relative tolerance |
|---|---|---|---|
| Non sensitized control group CT | 44 ± 4.9 | 0% | 100% |
| No pretreatment | 189.4 ± 4.6 | 100% | 0% |
| Peptide mixture 1 pretreatment | 124.2 ± 10.1 | 55% | 45% |
| Peptide mixture 2 pretreatment | 153.8 ± 13.3 | 76% | 24% |
| Peptide mixture 3 pretreatment | 109.7 ± 9.6 | 45% | 55% |
| NDO pretreatment | 172.1 ± 11.5 | 88% | 22% |
| NDO + peptide mixture 1 pretreatment | 73 ± 6.3* | 20% | 80% |
| NDO + peptide mixture 2 pretreatment | 159.2 ± 11.3 | 79% | 21% |
| NDO + peptide mixture 3 pretreatment | 97.4 ± 15.3 | 37% | 63% |

* $P < 0.05$ compared to non-pretreated group.

As can be seen from the results in table 5 intradermal ear challenge with whey induced a significant ear swelling at 1 hour in whey sensitized animals compared to non-sensitized mice ($p<0.01$). Ear swelling is an allergic response, and this response was slightly reduced when the preceding diet comprised prebiotics or peptide mixtures.

Mice pretreated with peptide mixture 1 showed a statistically significant less allergic response, indicating a tolerance inducing capacity. This induction of immune tolerance was synergistically enhanced when the preceding diet comprised also prebiotics, i.e. being much higher than expected based on the added effects based on peptide mixture 1 or NDO alone. Peptide mixtures 2 and 3 did not show these synergistic effects with NDO.

What is claimed is:
1. A method for inducing oral immune tolerance against dietary protein, said method comprising administering to a subject identified as having, or at risk of having, dietary protein allergy an enteral composition comprising at least one non-digestible oligosaccharide selected from the group consisting of fructo-oligosaccharide, non-digestible dextrin, galacto-oligosaccharide, xylo-oligosaccharide, arabino-oligosaccharide, arabinogalacto-oligosaccharide, gluco-oligosaccharide, glucomanno-oligosaccharide, galactomanno-oligosaccharide, mannan-oligosaccharide, chito-oligosaccharide, uronic acid oligosaccharide, sialyloligosaccharide and fuco-oligosaccharide and at least one partial protein hydrolysate, the partial protein hydrolysate comprising at least 3 wt. % of peptides with a size of 5 kDa or above and at least 50 wt. % of peptides with a size below 5 kDa and wherein the partial protein hydrolysate is partial mammalian milk protein hydrolysate, partial whey protein hydrolysate or partial beta-lactoglobulin hydrolysate, wherein the hydrolysate has not been subjected to fermentation, such that oral immune tolerance against dietary proteins is induced in said subject.

2. The method according to claim 1, wherein the composition comprises at least one beta-lactoglobulin peptide comprising a sequence selected from the group consisting of SEQ ID NO 1, SEQ ID NO 2, SEQ ID NO 3 and SEQ ID NO 4, and wherein the at least one beta-lactoglobulin peptide has a molecular weight below 5 kDa.

3. The method according to claim 1, wherein the size distribution of the peptides in the partial protein hydrolysate is 60 to 90%<1 kDa, 5 to 20% 1 to <2 kDa, 2 to 16% 2 to <5 kDa, 0.6 to 3% 5 to <10 kDa, 0.5 to 2% 10 to 20 kDa and 1 to 3% >20 kDa, based on dry weight of peptides present in partial protein hydrolysate.

4. The method according to claim 1, wherein the partial protein hydrolysate comprises a ratio of the relative amount (wt %) of peptides with a size from 2 to <5 kDa to the relative amount (wt %) of peptides with a size of at least 5 kDa is (5 to 1):1.

5. The method according to claim 1, wherein the non-digestible oligosaccharide is selected from the group consisting of fructo-oligosaccharide, galacto-oligosaccharide and uronic acid oligosaccharide.

6. The method according to claim 1, wherein the enteral composition comprises a protein component, a lipid component and digestible carbohydrates and wherein the protein component is present in an amount of 5 to 25% based on total calories of the composition.

7. The method according to claim 1, wherein the enteral composition comprises 0.05 to 20 wt. % non-digestible oligosaccharide based on dry weight of the composition.

8. The method according to claim 4 wherein, in the enteral composition, the ratio of the relative amount (wt %) of peptides with a size from 2 to <5 kDa to the relative amount (wt %) of peptides with a size of at least 5 kDa is (4 to 1):1.

9. The method according to claim 1, wherein the enteral composition is an infant formula or follow-on-formula.

10. A method for preventing inflammatory bowel disease, said method comprising administering to a subject identified as requiring prevention of inflammatory bowel disease an enteral composition comprising at least one non-digestible oligosaccharide selected from the group consisting of fructo-oligosaccharide, non-digestible dextrin, galacto-oligosaccharide, xylo-oligosaccharide, arabino-oligosaccharide, arabinogalacto-oligosaccharide, gluco-oligosaccharide, glucomanno-oligosaccharide, galactomanno-oligosaccharide, mannan-oligosaccharide, chito-oligosaccharide, uronic acid oligosaccharide, sialyloligosaccharide and fuco-oligosaccharide and at least one partial protein hydrolysate, the partial protein hydrolysate comprising at least 3 wt. % of peptides with a size of 5 kDa or above and at least 50 wt. % of peptides with a size below 5 kDa and wherein the partial protein hydrolysate is partial mammalian milk protein hydrolysate, partial whey protein hydrolysate or partial beta-lactoglobulin hydrolysate, wherein the hydrolysate has not been subjected to fermentation, such that inflammatory bowel disease is prevented in said subject.

11. The method according to claim 10, wherein the composition comprises at least one beta-lactoglobulin peptide comprising a sequence selected from the group consisting of SEQ ID NO 1, SEQ ID NO 2, SEQ ID NO 3 and SEQ ID NO 4, and wherein the at least one beta-lactoglobulin peptide has a molecular weight below 5 kDa.

12. The method according to claim 10, wherein the size distribution of the peptides in the partial protein hydrolysate is 60 to 90% <1 kDa, 5 to 20% 1 to <2 kDa, 2 to 16% 2 to <5 kDa, 0.6 to 3% 5 to <10 kDa, 0.5 to 2% 10 to 20 kDa and 1 to 3% >20 kDa, based on dry weight of peptides present in partial protein hydrolysate.

13. The method according to claim 10, wherein the partial protein hydrolysate comprises a ratio of the relative amount (wt %) of peptides with a size from 2 to <5 kDa to the relative amount (wt %) of peptides with a size of at least 5 kDa is (5 to 1):1.

14. The method according to claim 10, wherein the non-digestible oligosaccharide is selected from the group consisting of fructo-oligosaccharide, galacto-oligosaccharide and uronic acid oligosaccharide.

15. The method according to claim 10, wherein the enteral composition comprises a protein component, a lipid component and digestible carbohydrates and wherein the protein component is present in an amount of 5 to 25% based on total calories of the composition.

16. The method according to claim 10, wherein the enteral composition comprises 0.05 to 20 wt. % non-digestible oligosaccharide based on dry weight of the composition.

17. The method according to claim 13, wherein, in the enteral composition, the ratio of the relative amount (wt %) of peptides with a size from 2 to <5 kDa to the relative amount (wt %) of peptides with a size of at least 5 kDa is (4 to 1):1.

18. The method according to claim 10, wherein the enteral composition is an infant formula or follow-on-formula.

19. A method for inducing oral immune tolerance against cow's milk protein, said method comprising administering to a subject identified as having, or at risk of having, cow's milk protein allergy an enteral composition comprising at least one non-digestible oligosaccharide selected from the group consisting of fructo-oligosaccharide, non-digestible dextrin, galacto-oligosaccharide, xylo-oligosaccharide, arabino-oligosaccharide, arabinogalacto-oligosaccharide, gluco-oligosaccharide, glucomanno-oligosaccharide, galactomanno-oligosaccharide, mannan-oligosaccharide, chito-oligosaccharide, uronic acid oligosaccharide, sialyloligosaccharide and fuco-oligosaccharide and at least one partial protein hydrolysate, the partial protein hydrolysate comprising at least 3 wt. % of peptides with a size of 5 kDa or above and at least 50 wt. % of peptides with a size below 5 kDa and wherein the partial protein hydrolysate is partial mammalian milk protein hydrolysate, partial whey protein hydrolysate or partial beta-lactoglobulin hydrolysate, wherein the hydrolysate has not been subjected to fermentation, such that oral immune tolerance against cow's milk protein is induced in said subject.

20. The method according to claim 19, wherein the composition comprises at least one beta-lactoglobulin peptide comprising a sequence selected from the group consisting of SEQ ID NO 1, SEQ ID NO 2, SEQ ID NO 3 and SEQ ID NO 4, and wherein the at least one beta-lactoglobulin peptide has a molecular weight below 5 kDa.

21. The method according to claim 19, wherein the non-digestible oligosaccharide is selected from the group consisting of fructo-oligosaccharide, galacto-oligosaccharide and uronic acid oligosaccharide.

22. The method according to claim 19, for inducing oral immune tolerance against whey protein, said subject identified as having, or at risk of having, whey protein allergy.

23. The method according to claim 19, wherein the non-digestible oligosaccharide is a mixture of trans-galacto-oligosaccharide and fructo-oligosaccharide.

24. The method according to claim 1, wherein the non-digestible oligosaccharide is a mixture of trans-galacto-oligosaccharide and fructo-oligosaccharide.

* * * * *